United States Patent
Ivachtchenko

(10) Patent No.: US 8,895,613 B2
(45) Date of Patent: Nov. 25, 2014

(54) FLUOROSUBSTITUTED-(3R,4R,5S)-5-GUANIDINO 4-ACETAMIDO-3-(PENTAN-3-YLOXY)CYCLOHEX-1-ENECARBOXYLIC ACID COMPOUND, ESTER AND USE THEREOF

(71) Applicant: Asavi, LLC, Hallandale Beach, FL (US)

(72) Inventor: Alexandre Vasilievich Ivachtchenko, Encinitas, CA (US)

(*) Notice: Subject to any disclaimer, the term of this patent is extended or adjusted under 35 U.S.C. 154(b) by 0 days.

(21) Appl. No.: 13/872,174

(22) Filed: Apr. 29, 2013

(65) Prior Publication Data

US 2013/0303609 A1 Nov. 14, 2013

(51) Int. Cl.
*A01N 37/00* (2006.01)
*A61K 31/215* (2006.01)
*C07C 279/16* (2006.01)

(52) U.S. Cl.
CPC ........... *C07C 279/16* (2013.01); *C07C 2101/16* (2013.01)
USPC .............................. 514/529; 435/184; 560/34

(58) Field of Classification Search
USPC .............................. 514/529; 435/184; 560/34
See application file for complete search history.

(56) References Cited

U.S. PATENT DOCUMENTS 5,952,375 A * 9/1999 Bischofberger et al. ...... 514/459

OTHER PUBLICATIONS

STN Accession No. 2006:1238901, 2006.*
Patani et al, Chem. Rev. 1996, 96, 3147-3176.*
Ivachtchenko A.V., et al.: Novel oral anti-influenza drug candidate AV 5080. J. Antimicrob. Chemother. doi:10.1093/jac/dku074, Apr. 11, 2014.

* cited by examiner

*Primary Examiner* — Wu-Cheng Winston Shen
*Assistant Examiner* — Jean Cornet

(57) ABSTRACT

The present invention relates to novel neuraminidase activity inhibitors and use thereof for prophylaxis and treatment of influenza infection, that is to fluorosubstituted4-acetamido-5-guanidino-3-(pentan-3-yloxy)cyclohex-1-enecarboxylic acids and their esters of the general formula 1, pharmaceutically acceptable salts and/or hydrates thereof,

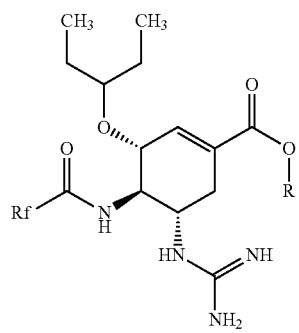

wherein R is hydrogen, an optionally substituted $C_1$-$C_5$alkyl, $C_2$-$C_5$alkenyl or $C_2$-$C_5$alkynyl; Rf is $CH_2F$ or $CHF_2$.

A pharmaceutical composition is provided, a method for its preparation, as well as a method for prophylaxis and treatment of viral diseases.

9 Claims, No Drawings

FLUOROSUBSTITUTED-(3R,4R,5S)-5-GUANIDINO 4-ACETAMIDO-3-(PENTAN-3-YLOXY)CYCLOHEX-1-ENECARBOXYLIC ACID COMPOUND, ESTER AND USE THEREOF

CROSS REFERENCE TO RELATED APPLICATIONS

This application is a National stage entry of Russian Federation application RU 2012119272 of May 12, 2012 which claims benefit of foreign priority to May 12, 2012. The priority application is hereby incorporated by reference in its entirety.

FIELD OF THE INVENTION

The present invention relates to novel compounds—fluorosubstituted (3R,4R,5S)-5-guanidino-4-acetamido-3-(pentan-3-yloxy)cyclohex-1-enecarboxylic acids and their esters—inhibitors of neuraminidase activity.

PRIOR ART

Many microorganisms comprising neuraminidase are pathogenic to human and such animals as poultry, horses, pigs and seals. These pathogenic microorganisms include influenza virus. Neuraminidase is associated with pathogenicity of influenza virus.

In this connection novel fluorosubstituted cyclohex-1-enecarboxylic acids and their esters are of primary concern as drug substances for medicaments intended for prophylaxis and treatment of influenza.

The known neuraminidase inhibitors are (3R,4R,5S)-5-amino-3-alkyloxy-4-acetamidocyclohex-1-enecarboxylic acids of the general formula A1, at that, the most active of them is (3R,4R,5S)-5-amino-4-acetamido-3-(pentan-3-yloxy)cyclohex-1-enecarboxylic acid of formula A2, which, as it was shown by X-ray diffraction data for its complex with neuraminidase of influenza virus, is effectively bound to the active center of enzyme (Oseltamivir Carboxylate) [C. U. Kim, W. Lew, M. A. Williams, et al. *J. Am. Chem. Soc.* 1997, 119, 681-690.].

Ethyl ester of Oseltamivir carboxylate A3, known as Oseltamivir Phosphate or Tamiflu (Oseltamivir Phosphate, Tamiflu) [J. C. Rohloff, K. M. Kent, M. J. Postich, et al. *J. Org. Chem.* 1998, 63, 4545.], is a medicamental precursor of Oseltamivir carboxylate A2.

It is also known (3R,4R,5S)-5-guanidino-4-trifluoroacetamido-3-(pentan-3-yloxy)cyclohex-1-enecarboxylic acid A4, exhibiting activity towards neuraminidase of influenza virus H5N1 [Q.-S. Du, R.-B. Huang, Y.-T. Wei, Z.-W. Pa, L.-Q. Du, K.-C. Chou. Fragment-Based Quantitative Structure-Activity Relationship (FB-QSAR) for Fragment-Based Drug Design. *J. Comput. Chem.* 2008, 30(2), 295-304].

It is also known 5-Acetamido-2,3-didehydro-3,4,5-trideoxy-4-guanidino-alpha-D-glycero-D-galacto-2-nonulopyranosonic acid (Zanamivir) with activity towards neuraminidase of influenza A and B viruses, as well as influenza A and B virus H1N1 [J. M. Woods, R. C. Bethell, J. A. Coates, et al. 4-Guanidino-2,4-dideoxy-2,3-dehydro-N-acetylneuraminic acid is a highly effective inhibitor both of the sialidase (neuraminidase) and of growth of a wide range of influenza A and B viruses in vitro. *Antimicrob Agents Chemother.* 1993, 37(7), 1473-1479].

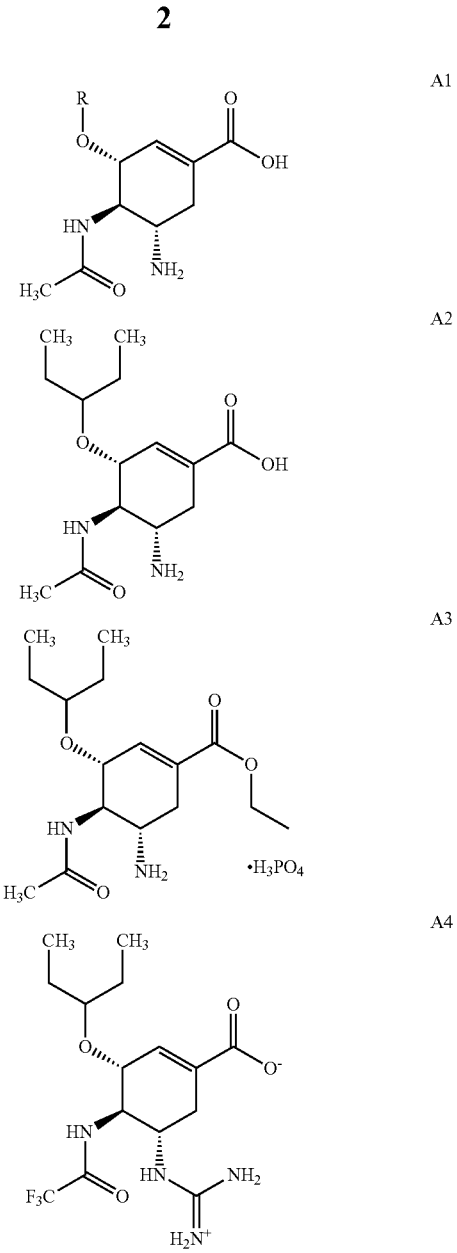

The search for highly effective anti-influenza medicaments exhibiting enhanced activity towards resistant influenza viruses still remains one of the main directions in developing novel pharmacological remedies for treating influenza. In this context, the development of novel anti-influenza ingredients, pharmaceutical compositions and medicaments, as well as methods for their preparation and use is of current interest.

DISCLOSURE OF THE INVENTION

In context of the invention, terms are generally defined as follows:

"Alkenyl" means an aliphatic straight or branched hydrocarbon chain, comprising 2-7 carbon atoms and including at least one carbon-carbon double bond. Branched means that a straight alkenyl chain contains one or more lower alkyl groups, such as methyl, ethyl or propyl. Alkyl group may have one or more substituents, for example, halogen, alkenyloxy, cycloalkyl, cyano, hydroxy, alkoxy, carboxy, alkynyloxy, aralkoxy, aryloxy, aryloxycarbonyl, alkylthio, heteroaralkyloxy, heterocyclyl, heterocyclylalkyloxy, alkoxycarbonyl, aralkoxycarbonyl, heteroaralkyloxycarbonyl or $R_k^a R_{k+1}^a N-$, $R_k^a R_{k+1}^a NC(=O)-$, $R_k^a R_{k+1}^a NSO_2-$, where $R_k^a$ and $R_{k+1}^a$ independently of each other represent "amino group substituents" the meanings of which are defined in this section, such as hydrogen, alkyl, aryl, aralkyl, heteroaralkyl, heterocyclyl or heteroaryl, or $R_k^a$ and $R_{k+1}^a$ together with the nitrogen atom they are attached to form through $R_k^a$ and $R_{k+1}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, benzyloxycarbonylmethyl and pyridylmethyloxycarbonylmethyl. The preferred alkenyl groups are ethenyl, propenyl, n-butenyl, iso-butenyl, 3-methylbut-2-enyl, n-pentenyl and cyclohexylbutenyl.

"Alkyl" means an aliphatic hydrocarbon straight or branched chain with 1-12 carbon atoms. Branched means the alkyl chain with at least one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k^a R_{k+1}^a N-$, $R_k^a R_{k+1}^a NC(=O)-$, $R_k^a R_{k+1}^a NC(=S)-$, $R_k^a R_{k+1}^a NSO_2-$, where $R_k^a$ and $R_{k+1}^a$ independently of each other represent "amino group substituents" the meanings of which are defined in this section, for example, hydrogen, alkyl, aryl, aralkyl, heteroaralkyl, heterocyclyl or heteroaryl, or $R_k^a$ and $R_{k+1}^a$ together with the N-atom, they are attached to, form through $R_k^a$ and $R_{k+1}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxycarbonylmethyl, ethoxycarbonylmethyl, benzyloxycarbonylmethyl and pyridylmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k^a R_{k+1}^a N-$, $R_k^a R_{k+1}^a NC(=O)-$, annelated arylheterocyclenyl and annelated arylheterocyclyl.

"Alkynyl" means an aliphatic hydrocarbon straight or branched chain with 2-12 carbon atoms including at least one carbon-carbon triple bond. Branched means that straight alkynyl chain contains at least one or more lower alkyl groups, such as methyl, ethyl or propyl. Alkyl group may have one or more substituents, for example, halogen, alkenyloxy, cyano, hydroxy, alkoxy, alkynyloxy, aralkoxy, aryloxy, aryloxycarbonyl, alkylthio, heteroaralkyloxy, heterocyclyl, heterocyclylalkyloxy, alkoxycarbonyl, aralkoxycarbonyl, heteroaralkyloxycarbonyl or $R_k^a R_{k+1}^a N-$, $R_k^a R_{k+1}^a NC(=O)-$, $R_k^a R_{k+1}^a NSO_2-$, where $R_k^a$ and $R_{k+1}^a$ independently of each other represent "amino group substituents" such as hydrogen, alkyl, aryl, aralkyl, heteroaralkyl, heterocyclyl or heteroaryl, or $R_k^a$ and $R_{k+1}^a$ together with the N-atom they are attached to form through $R_k^a$ and $R_{k+1}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, benzyloxycarbonylmethyl and pyridylmethyloxycarbonylmethyl. The referred alkynyl groups are ethynyl, propynyl, n-butynyl, 3-methylbut-1-ynyl, n-pentynyl, bute-1,3-diynyl and hexa-1,3,5-triynyl.

"Hydrate" means stoichiometric or nonstoichiometric compositions of compounds or their salts with water.

"Active component" (drug-substance) means a physiologically active compound of synthetic or other (biotechnological, vegetable, animal, microbe and so on) origins exhibiting pharmacological activity which is an active ingredient of pharmaceutical composition employing in production and preparation of medicaments.

"Medicament"—is a compound (or a mixture of compounds as a pharmaceutical composition) in the form of tablets, capsules, injections, ointments and other ready forms intended for restoration, improvement or modification of physiological functions in humans and animals, and for treatment and prophylaxis of diseases, for diagnostics, anesthesia, contraception, cosmetology and others.

"Neuraminidase" (sialidase, acylneuraminile hydrolase, or EC 3.2.1.18) is an enzyme usual for animals and a number of microorganisms. It represents glycohydrolase that cleaves the glycosidic linkages of neuraminic acids in glycoproteins, glycolipids and oligosaccharides. Many of the microorganisms comprising neuraminidase, are pathogenic to human and such animals as poultry, horses, pigs and seals. These pathogenic organisms include influenza virus. Neuraminidase is associated with influenza virus pathogenicity.

Presumably it contributes to elution of newly synthesized virions from infected cells and also to virus movement (owing to its hydrolase activity) through the mucus of respiratory tract.

"Pharmaceutical composition" means a composition comprising a compound of the general formula 1 and at least one of the components selected from the group consisting of pharmaceutically acceptable and pharmacologically compatible fillers, solvents, diluents, carriers, auxiliary, distributing and sensing agents, delivery agents, such as preservatives, filler, disintegrators, moisteners, emulsifiers, suspending agents, thickeners, sweeteners, flavouring agents, aromatizing agents, antibacterial agents, fungicides, lubricants, and prolonged delivery controllers, choice and suitable proportions of which depend on the type and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacant and their mixtures as well. Protection against action of microorganisms can be provided by various antibacterial and antifungal agents, such as, for example, parabens, chlorobutanole, sorbic acid, and similar compounds. Composition may also contain isotonic agents, such as, for example, sugar, sodium chloride, and similar compounds. Prolonged action of composition may be achieved by agents slowing down absorption of active ingredient, for example, aluminum monostearate and gelatine. Examples of suitable carriers, solvents, diluents and delivery agents include water, ethanol, polyalcohols and their mixtures, natural oils (such as olive oil) and organic esters (such as ethyl oleate) for injections. Examples of fillers are lactose, milk-sugar, sodium citrate, calcium carbonate, calcium phosphate and the like. Examples of disintegrators and distributors are starch, alginic acid and its salts, and silicates. Examples of suitable lubricants are magnesium stearate, sodium lauryl sulfate, talc and polyethylene glycol of high molecular weight. Pharmaceutical composition for peroral, sublingval, transdermal, intramuscular, intravenous, subcutaneous, local or rectal administration of active ingredient, alone or in combination with another active compound may be administered to human and animals in a standard administration form, or in a mixture with traditional pharmaceutical carriers. Suitable standard administration forms include peroral forms such as tablets, gelatin capsules, pills, powders, granules, chewing-gums and peroral solutions or suspensions; sublingval and transbuccal administration forms; aerosols; implants; local, transdermal, subcutaneous, intramuscular, intravenous, intra-nasal or intraocular forms and rectal administration forms.

"Pharmaceutically acceptable salt" means relatively non-toxic both organic and inorganic salts of acids and bases disclosed in this invention. Salts could be prepared in situ in the processes of synthesis, isolation or purification of compounds or they could be prepared specially. In particular, salts of bases could be prepared from purified base of the disclosed compound and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of such salts properties is given in: Berge S. M., et al., "Pharmaceutical Salts" J. Pharm. Sci., 1977, 66: 1-19). Salts of the disclosed acids may also be prepared by the reaction of purified acids specifically with suitable base; moreover, metal salts and amine salts may be synthesized too. Metal salts are the salts of sodium, potassium, calcium, barium, zinc, magnesium, lithium and aluminum; sodium and potassium salts being preferred. Suitable inorganic bases from which metal salts can be prepared are sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of the disclosed acid salts are amines and amino acids of sufficient basicity to produce stable salt suitable for medical purposes use (in particular, they are to have low toxicity). Such amines include ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as holine, tetramethylammonium, tetraethylammonium, and the like. Aminoacids may be selected from the main aminoacids—lysine, ornithine and agrinine.

The authors have found novel neuraminidase inhibitors representing unknown before fluoro substituted (3R,4R,5S)-4-acylamido-5-guanidino-3-(pentan-3-yloxy)cyclohex-1-enecarboxylic acids and their esters of the general formula 1 and pharmaceutically acceptable salts or hydrates thereof, wherein:
R is hydrogen, an optionally substituted $C_1$-$C_5$alkyl, $C_2$-$C_5$alkenyl or $C_2$-$C_5$alkynyl; an $C_1$-$C_5$alkyl, $C_2$-$C_5$alkenyl or $C_2$-$C_5$alkynyl optionally substituted with $C_3$-$C_6$cycloalkyl, phenyl, pyridyl, $C_1$-$C_3$alkoxy;
Rf is $CH_2F$ or $CHF_2$.

The novel compounds of the general formula 1, as the authors have unexpectedly found, are more effective inhibitors of influenza virus neuraminidase than their known analogues Oseltamivir carboxylate A2 and (3R,4R,5S)-5-guanidino-4-trifluoroacetamido-3-(pentan-3-yloxy)cyclohex-1-enecarboxylic acid of formula A4, among other things, more active towards neuraminidase of Oseltamivir resistant virus of A/Vladivostok/16/09 (H1N1) influenza. Thus, for example, Oseltamivir carboxylate A2 and (3R,4R,5S)-5-guanidino-4-(2-trifluoroacetamido)-3-(pentan-3-yloxy)-cyclohex-1-enecarboxylic acid A4, showed neuraminidase activity $IC_{50}$=0.8 nM (for A2) and $IC_{50}$=80 nM (for A4) towards virus A/California/04/09, respectively. Acids A2 and A4 exhibit low activity towards neuraminidase of Oseltamivir resistant virus of A/Vladivostok/16/09 ($IC_{50}$=830 nM for A2 and $IC_{50}$>1000 nM for A4). At the same time, unknown before (3R,4R,5S)-5-guanidino-4-fluoroacetamido-3-(pentan-3-yloxy)cyclohex-1-enecarboxylic acid 1.1 has neuraminidase activity towards A/California/04/09 virus corresponding to $IC_{50}$=0.2 nM (in other words, it is 4 times more active than A2 and more active than A4 by factor of 400); towards A/Vladivostok/16/09 virus novel acid 1.1 exhibits $IC_{50}$=4 nM, that is, it is more active than A2 by factor of 207, and quite surprising, more active than its known 4-(2-trifluoroacetamido) analogue in 250 times. (3R,4R,5S)-5-Guanidino-4-difluoroacetamido-3-(pentan-3-yloxy)cyclohex-1-enecarboxylic acid 1.4 in comparison with A2 and A4 analogues also exhibits higher neuraminidase activity: towards A/California/04/09 virus it corresponds to $IC_{50}$=0.3 nM (it is 2.7 times more active than A2 and 267 times more active than A4); towards virus A/Vladivostok/16/09—novel acid 1.4 has $IC_{50}$=7 nM (it is more active than A2 by factor of 118 and by factor of 140 than A4).

In comparison with the effectiveness of Oseltamivir carboxylate A2 the novel compounds of the general formula 1 as the authors have unexpectedly found, are also much more effective neuraminidase inhibitors of other influenza strains by factor of 5-259 (Table 1).

TABLE 1

Anti-neuraminidase activity of (3R,4R,5S)-5-guanidino-4-fluoroacetamido-3-(pentan-3-yloxy)cyclohex-1-enecarboxylic acid 1.1 and Oseltamivir carboxylate A2 on panel strains of influenza viruses.

| | Inhibitor No | | |
|---|---|---|---|
| | A2. | 1.1 | $IC^{A2}_{50}/$ |
| Virus | $IC_{50}$, nM (number of experiments) | | $IC^{1.1}_{50}$ |
| A/California/07/09 (H1N1) | 0.86 ± 0.42 (8) | 0.18 ± 0.08 (6) | 5 |
| A/Chiken/Rostov on Don/35/07/(H5N1) | 1.78 ± 0.09 (2) | 0.20 ± 0.00 (2) | 9 |
| A/Pert/261/2009 (H1N1 pdm09; 275Y) | 360 ± 87 (4) | 1.39 ± 0.38 (4) | 259 |
| B/Brisbane/60/2008 | 25.42 ± 0.51 (2) | 1.27 ± 0.14 (2) | 20 |
| B/Pert/211/2001 (197D) | 39.24 ± 2.44 (4) | 2.08 ± 0.71 (4) | 19 |
| B/Pert/211/2001 (197E) | 230.2 ± 62.6 (4) | 6.65 ± 0.90 (4) | 35 |

The novel compounds of the general formula 1, as author established, is also more effective inhibitors of influenza virus neuraminidase than the well known Zanamivir (Zan) (Table 2).

TABLE 2

Anti-neuraminidase activity of (3R,4R,5S)-5-guanidino-4-fluoroacetamido-3-(pentan-3-yloxy)cyclohex-1-enecarboxylic acid 1.1 and Zanamivir (Zan) A2 on panel strains of influenza viruses.

| | Inhibitor | | |
|---|---|---|---|
| | Zan | 1.1 | $IC^{Zan}_{50}/$ |
| Virus | $IC_{50}$, nM (number of experiments) | | $IC^{1.1}_{50}$ |
| A/California/07/09 (H1N1) | 0.26 ± 0.32 (6) | 0.18 ± 0.08 (6) | 1.4 |
| A/Aichi/2/69 (H3N2) | 0.60 ± 0.45 (6) | 0.69 ± 0.19 (6) | 0.9 |
| A/Chiken/Roston on Don/35/07/(H5N1) | 0.59 ± 0.07 (2) | 0.20 ± 0.00 (2) | 3 |
| A/Pert/265/2009 (H1N1; 275H) | 0.46 ± 0.07 (4) | 0.07 ± 0.05 (4) | 6.6 |
| B/Brisbane/60/2008 | 1.87 ± 0.02 (2) | 1.27 ± 0.14 (2) | 1.4 |
| B/Pert/211/2001 (197D) | 3.67 ± 0.20 (4) | 2.08 ± 0.71 (4) | 1.8 |
| B/Pert/211/2001 (197E) | 21.98 ± 5.88 (4) | 6.65 ± 0.90 (4) | 3.2 |

Finally, the authors found that in comparison with Oseltamivir carboxylate and Zanamivir the new compounds are more effective in MDCK cell culture towards influenza virus strains Ia/California/07/09 (H1N1) and highly pathogenic strain Ia/duck/MN/1525/81 (H5N1) (Table 3). In particular, (3R,4R,5S)-5-guanidino-4-fluoroacetamido-3-(pentan-3-yloxy)cyclohex-1-enecarboxylic acid 1.1 is more active than Oseltamivir carboxylate (A2) by factor of 13 and Zanamivir (Zan) by factor of 20 towards Ia/California/07/09 (H1N1) strain, and towards highly pathogenic strain Ia/duck/MN/1525/81 (H5N1) its activity is higher than that of Oseltamivir carboxylate and Zanamivir (Zan) in 24 and 16 times, respectively.

TABLE 3

Specific activity of (3R,4R,5S)-5-guanidino-4-fluoroacetamido-3-(pentan-3-yloxy)cyclohex-1-enecarboxylic acid 1.1 in cell culture MDCK towards virus strains Ia/California/07/09 (H1N1) and highly pathogenic strain Ia/duck/MN/1525/81 (H5N1) in comparison with Oseltamivir carboxylate (A2) and Zanamivir (Zan).

| | Influenza strain | | | |
|---|---|---|---|---|
| | H1N1 Ia/California/07/09 | | H5N1 Ia/duck/MN/1525/81 | |
| | Activity | | | |
| Compound | $IC_{50}$, μM | $IC_{50}/IC^{1.1}_{50}$ | $IC_{50}$, μM | $IC^{Zan}_{50}/IC^{1.1}_{50}$ |
| A2 | 9.9 | 16.3 | 77.5 | 24.2 |
| Zan | 16.0 | 20.5 | 51.2 | 16.0 |
| 1.1 | 0.78 | | 3.2 | |

According to the present invention the preferred compounds are the compounds of the general formula 1, wherein R is hydrogen, methyl or ethyl.

The best embodiment of the present invention is the compounds of the general formula 1, selected from the group consisting of: (3R,4R,5S)-5-guanidino-4-fluoroacetamido-3-(pentan-3-yloxy)cyclohex-1-enecarboxylic acid 1.1, methyl (3R,4R,5S)-5-guanidino-4-fluoroacetamido-3-(pentan-3-yloxy)cyclohex-1-enecarboxylate 1.2, ethyl (3R,4R,5S)-5-guanidino-4-fluoroacetamido-3-(pentan-3-yloxy)cyclohex-1-enecarboxylate 1.3, (3R,4R,5S)-5-guanidino-4-difluoroacetamido-3-(pentan-3-yloxy)cyclohex-1-enecarboxylic acid 1.4, methyl (3R,4R,5S)-5-guanidino-4-difluoroacetamido-3-(pentan-3-yloxy)cyclohex-1-enecarboxylate 1.5, and ethyl (3R,4R,5S)-5-guanidino-4-difluoroacetamido-3-(pentan-3-yloxy)cyclohex-1-enecarboxylate 1.6.

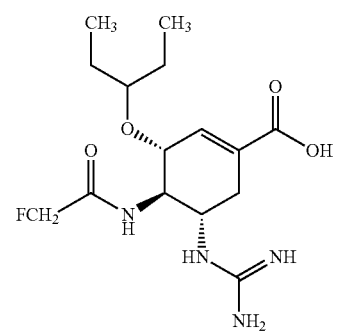

1.1

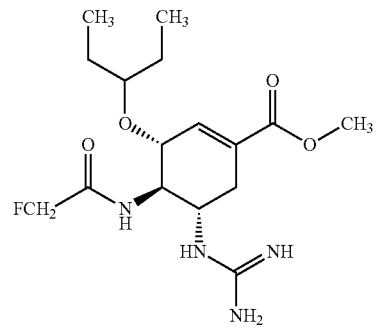

1.2

Neuraminidase inhibitors of influenza viruses of the general formula 1 could be prepared starting from alkyl 4-amino-5-(tert-butoxycarbonylamino)-3-(pentan-3-yloxy)cyclohex-1-enecarboxylate of the general formula 2 according to the scheme shown below.

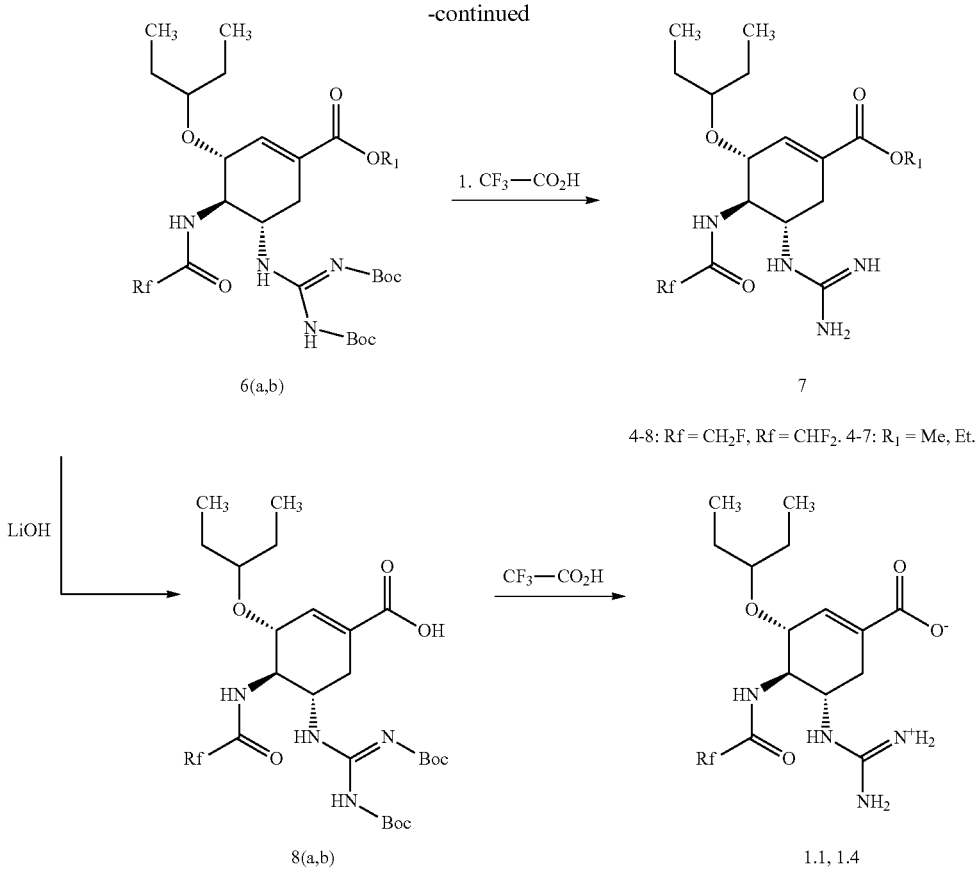

-continued

6(a,b) 7

4-8: Rf = $CH_2F$, Rf = $CHF_2$. 4-7: $R_1$ = Me, Et.

8(a,b) 1.1, 1.4

The novel neuraminidase inhibitors of influenza viruses representing unknown before (3R,4R,5S)-4-(2-fluoroacetamido)- and (3R,4R,5S)-4-(2,2-difluoroacetamido)-5-guanidino-3-(pentan-3-yloxy)cyclohex-1-enecarboxylic acids and their esters of the general formula 1 and their pharmaceutically acceptable salts also showed high anti-influenza activity in animal models of influenza pneumonia.

Anti-neuraminidase activity of the compounds was determined according to the method described in [WHO Collaborating Centre for Reference & Research on Influenza, Australia, Standard Operating Procedure WHO-025. Reviewed by: Aeron Hurt, Senior Scientist Review Date: Mar. 13, 2009].

According to the present invention novel compounds of the general formula 1 represent an active component for preparation of pharmaceutical compositions and final dosage forms for prophylaxis and treating influenza in warm-blooded animals and human.

The subject of the present invention is a pharmaceutical composition comprising as the active component compound of the general formula 1 or its pharmaceutically acceptable salts and/or hydrates in a therapeutically effective amount.

The pharmaceutical composition may include pharmaceutically acceptable excipients. Pharmaceutically acceptable excipients mean diluents, auxiliary agents and/or carriers applied in the sphere of pharmaceutics. According to the invention pharmaceutical composition together with the compound of the general formula 1 or its pharmaceutically acceptable salt and/or hydrate may include other active ingredients including those with anti-influenza activity, provided that they do not cause undesirable effects.

If needed, according to the present invention pharmaceutical compositions could be used in clinical practice in various forms prepared by mixing the said compositions with traditional pharmaceutical carries.

According to the present invention the carriers used in pharmaceutical compositions represent the carriers which are used in the sphere of pharmaceutics for preparation of commonly used forms. Binding agents, greasing agents, disintegrators, solvents, diluents, stabilizers, suspending agents, colorless agents, taste flavors are used for peroral forms; antiseptic agents, solubilizers, stabilizers are used in forms for injections; base materials, diluents, greasing agents, antiseptic agents are used in local forms.

The subject of the present invention is a method for preparation of pharmaceutical composition by mixing the therapeutically effective amount of at least one active component of the general formula 1 or its pharmaceutically acceptable salt and/or hydrate with inert filler and/or solvent.

The subject of the present invention is also a medicament exhibiting anti-influenza activity in the form of tablets, capsules or injections placed in a pharmaceutically acceptable packing intended for prophylaxis and treating influenza in human and warm-blooded animals and comprising a therapeutically effective amount of the novel active component of the general formula 1 or pharmaceutical composition comprising the novel active component of the general formula 1.

The subject of the present invention is also therapeutic kits for treating influenza including as one of the components the novel medicament or the novel pharmaceutical composition comprising as an active component, at least one compound of the general formula 1 or its pharmaceutically acceptable salt and/or hydrate.

According to the present invention, together with the novel medicament the therapeutic kit for treating influenza may include other known medicaments intended for treating influenza or medicaments reinforcing the immune system of patient.

According to the present invention one of embodiment is a method for prophylaxis or treating influenza or a disease, caused by influenza virus, in human and animals comprising administering a novel medicament, or a novel pharmaceutical composition or a novel therapeutic kit to a subject in need thereof.

Medicaments could be administered by means of inhalator, peroral or parenterally (for example, intravenous, subcutaneous, intraperitoneally or local). Clinical dose of active component of the general formula 1 can be corrected depending on: therapeutic efficiency and bio-accessibility of active ingredients in patients' organism, rate of their exchange and removal from organism, and age, gender, and severity of patient's symptoms. Thus, the daily intake for adults normally is 10~500 mg, preferably 50~300 mg. While preparing pharmaceutical composition as a dose unit the above effective dose is to be taken into consideration, at this each dose unit of composition contains 10~500 mg, preferably—50~300 mg. Following the instructions of physician or pharmacist, the medicaments may be taken several times over specified periods of time (preferably, from one to six times).

The subject of the present invention is also a method for inhibition of neuraminidase activity in vivo, including but not limited to neuraminidase of influenza virus, which comprises the step of contacting neuraminidase with a compound of the general formula 1.

BEST EMBODIMENT OF THE INVENTION

Below the invention is described by means of specific examples which illustrate, but not limit the scope of the invention.

Example 1

Preparation of (3R,4R,5S)-ethyl 4-(2,2-difluoroacetamido)-5-guanidino-3-(pentan-3-yloxy)cyclohex-1-enecarboxylate mesylate 1.6.CH3SO3H. To a solution of (3R,4R,5S)-ethyl 4-amino-5-(tert-butoxycarbonylamino)-3-(pentan-3-yloxy)cyclohex-1-enecarboxylate (2 g, 0.0054 mol, 1 eq), 1H-benzo[d][1,2,3]triazol-1-ol (0.867 g, 0.0065 mol, 1.2 eq), $N^1$-((ethylimino)methylene)-$N^2$,$N^2$-dimethylethane-1,2-diamine hydrochloride (1.239 g, 0.0065 mol, 1.2 eq) and diisopropylethylamine (2.212 g, 0.0178 mol, 3.3 eq) in THF (20 ml) 2,2-difluoroacetic acid 3b (0.624 g, 0.0065 mol, 1.2 eq) was added dropwise. The reaction mixture was stirred at room temperature for 4 h. Then solvents were evaporated in vacuo, residual oil was dissolved in ethyl acetate, washed with 5% $NaHCO_3$ solution, dried over $Na_2SO_4$, filtered and evaporated in vacuo. Yield of (3R,4R,5S)-ethyl 5-(tert-butoxycarbonylamino)-4-(2,2-difluoroacetamido)-3-(pentan-3-yloxy)cyclohex-1-enecarboxylate 4b is 89% (2.15 g). LCMS (M+H): found 449; calculated 448.51. The prepared product 4b (2.15 g, 0.0048 mol) was dissolved in 10% solution of trifluoroacetic acid in methylene chloride (20 ml) and stirred at room temperature for 12 h. Then solvents were evaporated in vacuo, residual oil was dissolved in ethyl acetate, washed with 5% $NaHCO_3$ solution, dried over $Na_2SO_4$, filtered and evaporated in vacuo. Yield of the product is 96% (1.605 g). Additional purification is carried out by means of column chromatography—eluent ethyl acetate/THF or by recrystallization from hexane. It gives (3R,4R,5S)-ethyl 5-amino-4-(2,2-difluoroacetamido)-3-(pentan-3-yloxy)cyclohex-1-enecarboxylate 5b, which was dissolved in methylene chloride and equivalent amount of methanesulfonic acid was added. In 10 min the solvent was evaporated, the obtained product was washed with hexane and dried in vacuo. Yield of mesylate 5b.$CH_3SO_3H$ is 90%. LCMS (M+H): found 349; calculated 348.39. $^1H$ NMR (DMSO-$d_6$), 400 MHz: 8.91 (d, J=13.2 Hz, 1H), 7.83 (br, 3H), 6.74 (s, 1H), 6.22 (t, J=54 Hz, 1H), 4.31 (d, J=8.4 Hz, 1H), 4.16 (q, J=7.2 Hz, 2H), 3.45 (m, 1H), 3.15 (dd, $J_1$=11.2 Hz, $J_2$=8.8 Hz, 1H), 2.59 (dd, $J_1$=18 Hz, $J_2$=6 Hz, 1H), 2.38 (m, 1H), 2.31 (s, 3H), 1.66 (m, 1H), 1.57 (m, 1H), 1.47 (m, 1H), 1.39 (m, 1H), 1.22 (t, J=7.6 Hz, 3H), 0.891 (t, J=7.2 Hz, 3H), 0.842 (t, J=7.2 Hz, 3H). To a solution of (3R,4R,5S)-ethyl 5-amino-4-(2,2-difluoroacetamido)-3-(pentan-3-yloxy)cyclohex-1-enecarboxylate 5b (1.6 g; 0.004598 mol; 1 eq) in DMF (16 ml) cooled in ice bath were subsequently added triethylamine (2.57 g; 0.0253 mol; 5.5 eq), N,N'-di-boc-thiourea (0.00505 mol; 1.35 g; 1.1 eq) and mercury chloride(II) (0.0055 mol; 1.49 g; 1.2 eq). The obtained mixture was stirred at cooling in ice bath for 1.5 h. After the reaction was completed the solid was filtered through celite, DMF was evaporated in vacuo, the residual oil was dissolved in ethyl acetate, washed with 5% $NaHCO_3$ solution, dried over $Na_2SO_4$, filtered and evaporated in vacuo. It gives 1.82 g (67%) of (3R,4R,5S)-ethyl 5-((Z)-2,3-bis(tert-butoxycarbonyl)guanidino)-4-(2,2-difluoroacetamido)-3-(pentan-3-yloxy)cyclohex-1-enecarboxylate 6b. LCMS (M+H): found 591; calculated 590.67. The solution of (3R,4R,5S)-ethyl 5-((Z)-2,3-bis(tert-butoxycarbonyl)guanidino)-4-(2,2-difluoroacetamido)-3-(pentan-3-yloxy)cyclohex-1-enecarboxylate 6b (1.82 g; 0.00308 mol) in 10% solution of trifluoroacetic acid in methylene chloride (20 ml) was stirred at room temperature for 12 h. Then the solvent was evaporated in vacuo, residual oil was dissolved in ethyl acetate, washed with 5% $NaHCO_3$ solution, dried over $Na_2SO_4$, filtered and evaporated in vacuo. It gives 1.1 g (92%) of (3R,4R,5S)-ethyl 4-(2,2-difluoroacetamido)-5-guanidino-3-(pentan-3-yloxy)cyclohex-1-enecarboxylate 1.6. To a solution of the prepared product in methylene chloride equivalent amount of metanesulfonic acid was added. In 10 min the solvent was evaporated, the product was washed with hexane and dried in vacuo. It gives mesylate of (3R,4R,5S)-ethyl 4-(2,2-difluoroacetamido)-5-guanidino-3-(pentan-3-yloxy) cyclohex-1-enecarboxylate 1.6.$CH_3SO_3H$, yield 95%. LCMS (M+H): found 391; calculated 390.43. $^1H$ NMR (DMSO-$d_6$), 400 MHz: 8.67 (d, J=8.4 Hz, 1H), 7.63 (d, J=9.6 Hz, 1H), 6.65 (s, 1H), 6.27 (t, J=53.6 Hz, 1H), 4.14 (q, J=7.2 Hz, 2H), 4.12 (m, 7H), 3.54 (m, 1H), 3.41 (m, 1H), 2.6 (m, 1H), 2.36 (s, 3H), 1.66 (m, 1H), 1.44 (m, 4H), 1.22 (t, J=7.2 Hz, 3H), 0.856 (t, J=7.6 Hz, 3H), 0.795 (t, J=7.6 Hz, 3H).

In a similar way compound 1.7—allyl (3R,4R,5S)-5-guanidino-4-(2,2-difluoroacetamido)-3-(pentan-3-yloxy)cyclohex-1-enecarboxylate (LCMS (M+H): found 354; calculated 353.44, towards A/California/04/09 virus $IC_{50}$<1 nM) and compound 1.8—prop-2-ynyl (3R,4R,5S)-5-guanidino-4-(2,2-difluoroacetamido)-3-(pentan-3-yloxy)cyclohex-1-enecarboxylate (LCMS (M+H): found 352; calculated 351.42, towards A/California/04/09 virus $IC_{50}$<1 nM), were prepared when (3R,4R,5S)-allyl-4-amino-5-(tert-butoxycarbonylamino)-3-(pentan-3-yloxy)cyclohex-1-enecarboxylate and (3R,4R,5S)-prop-2-ynyl-4-amino-5-(tert-butoxycarbonylamino)-3-(pentan-3-yloxy)cyclohex-1-enecarboxylate were used as starting materials (as compound 2), respectively.

Using the corresponding (3R,4R,5S)-4-amino-5-(tert-butoxycarbonylamino)-3-(pentan-3-yloxy)cyclohex-1-enecarboxylate as a starting material (compound 2) the following compounds were prepared:

2-cyclohexyl (3R,4R,5S)-5-guanidino-4-(2,2-difluoroacetamido)-3-(pentan-3-yloxy)cyclohex-1-enecarboxylate 1.9 (LCMS (M+H): found 460; calculated 459.55, $IC_{50}$<1 nM towards A/California/04/09 virus;

2-phenylethyl (3R,4R,5S)-5-guanidino-4-(2,2-difluoroacetamido)-3-(pentan-3-yloxy)cyclohex-1-enecarboxylate 1.10 (LCMS (M+H): found 454; calculated 453.51, $IC_{50}$<1 nM towards A/California/04/09 virus;

2-pyridin-3-ylethyl (3R,4R,5S)-5-guanidino-4-(2,2-difluoroacetamido)-3-(pentan-3-yloxy)cyclohex-1-enecarboxylate 1.11 (LCMS (M+H): found 455; calculated 454.49, $IC_{50}$<1 nM towards A/California/04/09 virus);

2-methoxyethyl (3R,4R,5S)-5-guanidino-4-(2,2-difluoroacetamido)-3-(pentan-3-yloxy)cyclohex-1-enecarboxylate 1.12 (LCMS (M+H): found 422; calculated 421.46, $IC_{50}$<1 nM towards A/California/04/09 virus).

Example 2

Mesylate of (3R,4R,5S)-ethyl 4-(2-fluoroacetamido)-5-guanidino-3-(pentan-3-yloxy)cyclohex-1-enecarboxylate 1.3.$CH_3SO_3H$ was prepared according to the procedure given in example 1 using monofluoroacetic acid as acylating agent. LCMS (M+H): found 373; calculated 372.44.

Example 3

(3R,4R,5S)-4-(2,2-difluoroacetamido)-5-guanidino-3-(pentan-3-yloxy)cyclohex-1-enecarboxylic acid 1.4. To a solution of (3R,4R,5S)-ethyl 5-((Z)-2,3-bis(tert-butoxycarbonyl)guanidino)-4-(2,2-difluoroacetamido)-3-(pentan-3-yloxy)cyclohex-1-enecarboxylate 6b (250 mg) in dioxane (5 ml) 5% solution of lithium hydroxide (2.5 ml) was added and the reaction mixture was stirred at room temperature for 45 min. Then lithium hydroxide was passivated by adding acetic acid (300 mcl), the solvents were evaporated in vacuo. The solid was extracted with isopropyl alcohol, the extract was dried over $Na_2SO_4$ and evaporated in vacuo. It gives (3R,4R,5S)-5-((Z)-2,3-bis(tert-butoxycarbonyl)guanidino)-4-(2,2-difluoroacetamido)-3-(pentan-3-yloxy)cyclohex-1-enecarboxylic acid 8b (200 mg, 84%). LCMS (M+H): found 563; calculated 562.62. The obtained acid 8b (200 mg) was dissolved in 10% solution of trifluoroacetic acid in methylene chloride (2 ml) and stirred at room temperature for 12 h. Then the solvents were evaporated in vacuo. (3R,4R,5S)-4-(2,2-Difluoroacetamido)-5-guanidino-3-(pentan-3-yloxy)cyclohex-1-enecarboxylic acid 1.4 was separated by HPLC method. LCMS (M+H): found 363; calculated 362.28. $^1$H NMR (DMSO-$d_6$), 400 MHz: 8.68 (d, J=8.4 Hz, 1H), 7.6 (d, J=10 Hz, 1H), 7.26 (br, 2H), 6.91 (br, 2H), 6.63 (s, 1H), 6.27 (t, J=53.6 Hz, 1H), 4.18 (d, J=8 Hz, 2H), 4.09 (m, 1H), 3.54 (q, J=10 Hz, 1H), 3.39 (m, 2H), 2.57 (dd, $J_1$=18 Hz, $J_2$=6 Hz, 1H), 2.31 (m, 1H), 1.44 (m, 4H), 0.85 (t, J=8 Hz, 3H), 0.795(t, J=7.6 Hz, 3H).

Example 4

(3R,4R,5S)-4-(2-fluoroacetamido)-5-guanidino-3-(pentan-3-yloxy)cyclohex-1-enecarboxylic acid 1.1 was prepared according to the procedure given in example 3. LCMS (M+H): found 345; calculated 345. $^1$H NMR (DMSO-$d_6$), 400 MHz: 8.16 (d, J=10 Hz, 1H), 7.56 (d, J=9.6 Hz, 1H), 6.64 (s, 1H), 4.80 (d, J=47.3 Hz, 2H), 4.21 (d, J=8.4 Hz, 1H), 3.89 (q, J=10.4 Hz, 1H), 3.71 (m, 1H), 2.67 (m, 1H), 2.25 (m, 1H), 1.42 (m, 4H), 0.85 (t, J=7.2 Hz, 3H), 0.78 (t, J=7.2 Hz, 3H).

Example 5

Mesylate of (3R,4R,5S)-methyl 4-(2-fluoroacetamido)-5-guanidino-3-(pentan-3-yloxy)cyclohex-1-enecarboxylate 1.2.$CH_3SO_3H$ was prepared according to the procedure given in example 1 using (3R,4R,5S)-methyl 4-amino-5-(tert-butoxycarbonylamino)-3-(pentan-3-yloxy)cyclohex-1-enecarboxylate as starting material and monofluoroacetic acid as acylating agent. LCMS (M+H): found 359; calculated 358.42.

Example 6

Mesylate of (3R,4R,5S)-methyl 4-(2,2-difluoroacetamido)-5-guanidino-3-(pentan-3-yloxy)cyclohex-1-enecarboxylate 1.5.$CH_3SO_3H$ was prepared according to the procedure given in example 1 using (3R,4R,5S)-methyl 4-amino-5-(tert-butoxycarbonylamino)-3-(pentan-3-yloxy)cyclohex-1-enecarboxylate as a starting material and difluoroacetic acid as acylating agent. LCMS (M+H): found 373; calculated 372.44.

Example 7

Preparation of pharmaceutical composition in tablet form. Starch (1600 mg), grained lactose (1600 mg), talcum (400 mg) and (3R,4R,5S)-4-(2-fluoroacetamido)-5-guanidino-3-(pentan-3-yloxy)cyclohex-1-enecarboxylic acid 1.1 (1000 mg) were carefully mixed together and pressed into a brick. The prepared brick was crushed into granules and riddled through sieves, gathering granules of 14-16 mesh size. The obtained granules were tableted into tablets of suitable form of 560 mg by weight each.

Example 8

Preparation of pharmaceutical composition in capsule form. (3R,4R,5S)-4-(2-Fluoroacetamido)-5-guanidino-3-(pentan-3-yloxy)cyclohex-1-enecarboxylic acid 1.1 was carefully mixed with a powder of lactose in ratio 2:1. The prepared powdery mixture was packed on 300 mg into gelatinous capsules of suitable size.

Example 9

Preparation of pharmaceutical composition in the form of injections for intramuscular, intraperitoneal or subcutaneous injections. (3R,4R,5S)-4-(2-Fluoroacetamido)-5-guanidino-3-(pentan-3-yloxy)cyclohex-1-enecarboxylic acid 1.1 (500 mg) was mixed with chlorobutanol (300 mg), propylene glycol (2 ml) and injectable water (100 ml). The resultant solution was filtered and placed into 1 ml ampoules which were sealed.

Example 10

Determination of activity of compounds of the general formula 1 towards neuraminidase of influenza virus. In preliminary experiments working dilutions for strains of allantoic viruses of influenza A/California/07/09 (H1N1) and A/Aichi/2/69 (H3N2) as well as for resistant influenza virus A/Vladivostok/16/09 (H1N1) which was prepared in oseltamivir cell culture were determined. For this purpose by 60 µl of each virus 2-fold diluted on the reaction buffer mixture (RBM, 50 mM MES, 5 mM $CaCl_2$, pH 6.5) were prepared in 96-well plate with a round bottom. From this plate by 50 µl of 2-fold diluted virus was transferred into 96-well plates with flat bottom for fluorescence measurement (FluoroNunc, black, kat. No. 237105), then, equal volume of substrate buffer (SB, 12.5 mM 2'-(4-methylumbelliferyl)-α-D-N-acetylneuraminic acid, Sigma, 40 mM of acetate buffer pH=5.8) was added to them. As a control there were used the wells to which by 50 µl of RBM were added instead of virus. After incubation of the plate at gentle shaking for 1 h at 37°, 100 µl of stop-solution (2.225 mL of 0.824M NaOH in 11.0 mL of ethanol) was added to each well, that was followed by measurement of fluorescence at $\lambda_{ex}$=360 nm and $\lambda_{em}$=448 nm using Varioskan Flach (Thermo Scientific) instrument. For further work those virus dilutions were chosen, which corresponded to the middle of the linear section of virus dilution-fluorescence value curve. Determination of anti-neuraminidase activity of compounds was carried out in 96-well plates with flat bottom for fluorescence measurement (FluoroNunc, black, kat. No. 237105). For this purpose dilutions (50 µl, prepared with RBM) of the disclosed compounds and their analogous of formulas A2 and A4 were added to the wells of rows from B to H (used concentrations—0.03; 0.3; 3; 30; 300; 3000; 30000 nM—each concentration on a row). As virus control the wells of A row were used to which instead of virus the equal volume (50 µl) of RBM was added. Then to the corresponding wells by 50 µl of chosen working dilutions with RBM of each virus were added. As a control the wells were used to which instead of virus the equal volume of RBM was added. After stirring and incubation at room temperature for 45 min to all the wells the equal volume of RBM was added. After repeated stirring and incubation of the планшета at 37° for 1 h stop-solution in amount of 100 µl was added to each well. Measurement of fluorescence was made at $\lambda_{ex}$=360 nm and $\lambda_{em}$=448 nm with the use of Varioskan Flach (Thermo Scientific) instrument. All determinations were carried out at least in duplicate (two wells of the plate). The percentage of inhibition of neuraminidase activity by tested compound of the general formula 1 was calculated by the formula: inhibition %=100−(SUF experiment−SUF control/SUF virus control in the absence of compound−SUF control), where SUF is a standard unit of fluorescence). The percentage of inhibition of neuraminidase activity by tested compound of the general formula 1 was calculated by the formula: inhibition %=100−(SUF experiment−SUF control/SUF virus control in the absence of compound−SUF control), where SUF is a standard unit of fluorescence). The concentration of compound at which SUF value was reduced by 50% was taken as inhibitory concentration 50 $IC_{50}$.

Example 11

Investigation of anti-influenza activity of compounds of the general formula 1 (1.1, 1.3, 1.4 and 1.6) on a model of influenza pneumonia in mice. Pre-weighted mice (female non-linear, average weight 12-15 g) were infected with influenza virus A/Aichi/2/69 (H3N2) (10 $LD_{50}$ in 50 µl) intranasally under light ether anesthesia. Determination of $LD_{50}$ was carried out in a preliminary experiment by means of allantoic virus titration using the same mice that were then used in the main experiment. The following scheme of treatment was used: animals were injected twice 24 h and 1 h before infection, in 24 h after infection and then 1 time a day during the following 5 days. For oral administration disposable insulin syringe with a special needle (lavage) was used; effect of the following doses was investigated: 25 mg/kg/day of each compound in a volume of 100 µl. As a reference compound was used Tamiflu in doses ranging from 5 mg/kg/day to 30 mg/kg/day. There were 10 animals in the group of "virus control", as well as in each group of animals "treated with compounds" of the general formula 1 or Tamiflu of formula A3. The "treated" and control animals were observed daily; during the first 5 days after infection they were weighed every day, further—in a day. Chemotherapeutic activity of compounds on the model of influenza pneumonia in mice was estimated by an index-number of protection against lethal viral infection and by weight loss in the groups of animals treated with the tested compounds in comparison with weight of animals in control group. Lowering or increasing of weight was calculated for each mouse separately and expressed in percentage. The weight of animal before infection was taken as 100%. For all animals of one group the average percentage of weight loss as well as weight gain was determined.

In a preliminary experiment a dose of virus containing 10 $LD_{50}$ in volume of 100 µl was determined. Then all animals of the group were infected with this dose. Effectiveness of the compounds of the general formula 1 on the model of influenza pneumonia in mice was estimated by the number of animals survived after virus infection, by average life expectancy and weight change of infected animals.

It was found that on the 7-th day of observation all the mice infected with virus and not treated with tested compounds ("virus control" group) died.

The conducted experiments showed that by the time when the last animal of "virus control" group died, death of animals treated with compounds of the general formula 1 and Tamiflu ("treated with compounds") was prevented completely.

Anti-influenza action of the tested compounds of the general formula 1 and Tamiflu of formula A3 consists in slowing down the weight losses in groups of "treated mice" in comparison with the group of "virus control". Weight loss of animal is one of the clinical implications of influenza pneumonia. The larger weight loss of the animal is an evidence of a more severe course of disease. Weighing of mice was carried out on the 1, 2, 3, 4 and 5 days after infection, then every other day up to the 15 day of observation. It was found that for animals of "virus control" group the most weight loss was observed on the 5-th day after infection (about 10%). In the contrast with the animals of "virus control" group the animals treated with compounds of the general formula 1 and Tamiflu, on an average, did not lose weight. Starting with the 9$^{th}$ day all the animals of "treated groups" extensively and steadily gained weight.

Thus, high efficiency of treating influenza pneumonia in mice with compounds of formulas 1.1, 1.3, 1.4 and 1.6 has been shown.

INDUSTRIAL APPLICABILITY

The present invention could be used in medicine, veterinary, biochemistry.

The invention claimed is:
1. A fluorosubstituted (3R,4R,5S)-4-acylamido-5-guanidino-3-(pentan-3-yloxy)cyclohex-1-enecarboxylic acid compound of general formula 1, or a pharmaceutically acceptable salt or hydrate thereof,

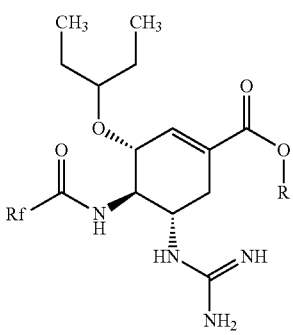

wherein:
R is hydrogen, an optionally substituted $C_1$-$C_5$alkyl, $C_2$-$C_5$alkenyl or $C_2$-$C_5$alkynyl;
Rf is $CH_2F$ or $CHF_2$.

2. The compound of claim 1, wherein R is hydrogen, methyl or ethyl.

3. The compound of claim 1 selected from the group consisting of:
(3R,4R,5S)-5-guanidino-4-fluoroacetamido-3-(pentan-3-yloxy)cyclohex-1-enecarboxylic acid;
methyl (3R,4R,5S)-5-guanidino-4-fluoroacetamido-3-(pentan-3-yloxy)cyclohex-1-enecarboxylate,
ethyl (3R,4R,5S)-5-guanidino-4-fluoroacetamido-3-(pentan-3-yloxy)cyclohex-1-enecarboxylate;
(3R,4R,5S)-5-guanidino-4-difluoroacetamido-3-(pentan-3-yloxy)cyclohex-1-enecarboxylic acid;
methyl (3R,4R,5S)-5-guanidino-4-difluoroacetamido-3-(pentan-3-yloxy)cyclohex-1-enecarboxylate; and
ethyl (3R,4R,5S)-5 -guanidino-4-difluoroacetamido-3-(pentan-3-yloxy)cyclohex-1-enecarboxylate.

4. An active component exhibiting inhibitory activity towards neuraminidase Of an influenza virus comprising a compound of claim 1.

5. A pharmaceutical composition, exhibiting inhibitory activity towards neuraminidase of an influenza virus, for treating influenza comprising a therapeutically effective amount of an active component as claimed in claim 4 and at least one pharmaceutically acceptable excipient.

6. The pharmaceutical composition of claim 5 in the form of a tablet, a capsule or an injection placed in a pharmaceutically acceptable package.

7. The pharmaceutical composition of claim 5 for treating influenza virus mediated pneumonia.

8. A method for inhibition of neuraminidase activity comprising contacting a neuraminidase with a compound of claim 1, wherein the neuraminidase is neuraminidase of an influenza virus.

9. A method for treating influenza comprising administering a therapeutically effective amount of an active ingredient as claimed in claim 4 or a pharmaceutical composition as claimed in any of claims 5-7 to a subject in need thereof.

* * * * *